(12) United States Patent
Bell et al.

(10) Patent No.: US 8,413,490 B2
(45) Date of Patent: Apr. 9, 2013

(54) MODULAR UNDERWATER SAMPLING APPARATUS

(75) Inventors: Ryan J. Bell, Pinellas Park, FL (US); R. Timothy Short, St. Petersburg, FL (US); Strawn K. Toler, Bradenton, FL (US); Bill Huzar, Palm Harbor, FL (US)

(73) Assignee: SRI International, Menlo Park, CA (US)

( * ) Notice: Subject to any disclaimer, the term of this patent is extended or adjusted under 35 U.S.C. 154(b) by 697 days.

(21) Appl. No.: 12/558,337

(22) Filed: Sep. 11, 2009

(65) Prior Publication Data

US 2010/0064825 A1    Mar. 18, 2010

Related U.S. Application Data

(60) Provisional application No. 61/096,694, filed on Sep. 12, 2008.

(51) Int. Cl.
*G01N 1/14* (2006.01)
*G01N 35/10* (2006.01)

(52) U.S. Cl.
USPC .................. 73/64.56; 73/863.11; 73/864.35; 73/864.21; 73/864.22

(58) Field of Classification Search ............ 73/64.56, 73/863.02–863.11, 863.32, 863.83, 864.21–864.22, 73/864.35; 422/68.1; 250/288
See application file for complete search history.

(56) References Cited

U.S. PATENT DOCUMENTS

| 3,587,670 | A | * | 6/1971 | Brailsford ................. 73/864.35 |
| 5,356,458 | A | * | 10/1994 | Javadi et al. ........... 73/864.34 X |
| 5,466,604 | A | * | 11/1995 | Yang et al. ................. 435/286.1 |
| 5,552,319 | A | * | 9/1996 | Yang et al. ................. 435/286.5 |
| 5,643,799 | A | * | 7/1997 | Atwater et al. ............... 436/133 |
| 5,925,572 | A | * | 7/1999 | Byrne et al. .................. 436/163 |
| 6,143,246 | A | * | 11/2000 | Lee et al. ................. 422/68.1 X |
| 2010/0070201 | A1 | * | 3/2010 | Bell et al. ......................... 702/30 |

OTHER PUBLICATIONS

Kevin W. Mandernack et al, In situ sulfide removal and CO2 fixation rates at deep-sea hydrothermal vents and the oxic/anoxic interface in Framvaren Fjord, Norway, 1999, Marine Chemistry 66, pp. 201-213.*

* cited by examiner

*Primary Examiner* — Thomas P Noland

(57) ABSTRACT

The present invention relates generally to an apparatus for obtaining a sample underwater. In one embodiment, the apparatus includes a syringe pump comprising a plurality of syringes, a sampling probe coupled to the syringe pump for collecting the sample underwater and an analyzer module coupled to the syringe pump.

12 Claims, 5 Drawing Sheets

MODULAR UNDERWATER SAMPLING APPARATUS

CROSS REFERENCE TO RELATED APPLICATIONS

This application claims the benefit of U.S. Provisional Application No. 61/096,694, filed on Sep. 12, 2008, which is herein incorporated by reference in its entirety.

REFERENCE TO GOVERNMENT FUNDING

This application was made with Government support under contract no. N00014-07-C-0720 awarded by the Office of Naval Research, and contract no. OCE-0536345 awarded by the National Science Foundation. The Government has certain rights in this invention.

FIELD OF THE INVENTION

The present invention relates generally to underwater sampling of a water column and sediment pore water in seawater or freshwater, and more specifically to a modular underwater sampling apparatus.

BACKGROUND OF THE INVENTION

Devices that sample pore water in sediments require pumps with precisely controlled flow rates, often less than 1 ml/min. Some devices use a variety of piston pumps to draw samples to an analyzer or collection device. However, piston pumps are not dependable to provide a constant flow rate for extended periods of time, especially at low flow rates against varying resistance, and they suffer from pulsation of the flow stream.

Osmotic pumps require no electrical power. They are based on the osmotic pressure differential between seawater and saturated salt solutions. However, osmotic pumps cannot be turned on and off, have extremely low flow rates that cannot be effectively controlled.

In addition, currently used underwater sampling devices cannot perform some analyses in-situ. Rather, the sample must be transported to a remote location for performing further analysis. This leads to the possibility of contamination of the sample or loss of analytes, particularly in the case of highly reactive or volatile species.

SUMMARY OF THE INVENTION

In one embodiment, the present invention is directed towards an apparatus for obtaining a sample underwater. In one embodiment, the apparatus comprises a syringe pump comprising a plurality of syringes, a sampling probe coupled to said syringe pump for collecting said sample underwater and an analyzer module coupled to said syringe pump.

In one embodiment, the present invention is directed towards a syringe pump for obtaining a sample underwater. The syringe pump for obtaining a sample underwater comprises an oil filled box, a plurality of motors coupled to said oil filled box, a plurality of syringes, wherein each one of said plurality of syringes is coupled to one of said plurality of motors and a sampling probe coupled to at least one of said plurality of motors for collecting said sample underwater.

In one embodiment, the present invention is directed towards an apparatus for underwater sampling. The apparatus for obtaining a sample underwater comprises an analyzer module and means for providing a sample to said analyzer module at a flow rate of approximately 0.001 milliliters (mL) per minute (min) to 20.0 mL/min.

BRIEF DESCRIPTION OF THE DRAWINGS

The teaching of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present invention provides a modular underwater sample pump and probe that utilizes in-situ mass spectrometry. As a result, porewater or water in sediment may be collected and analyzed in situ for a variety of compounds such as dissolved gases and volatile organic compounds (VOCs). That is, the sample does not need to be sent to a remote off-site laboratory for analysis.

In addition, the modularity of the underwater sample pump and probe provides flexibility depending on what type of sampling is desired or needs of a particular application. For example, the syringes may be changed to adjust flow rates to the mass spectrometer, the number of syringes may be changed or the type of analyzer may be changed based on the desired application, and so forth. A sampling probe for pore water in sediments may be substituted for one of the syringes, and the probe may be altered for other analyses.

Figure 1:
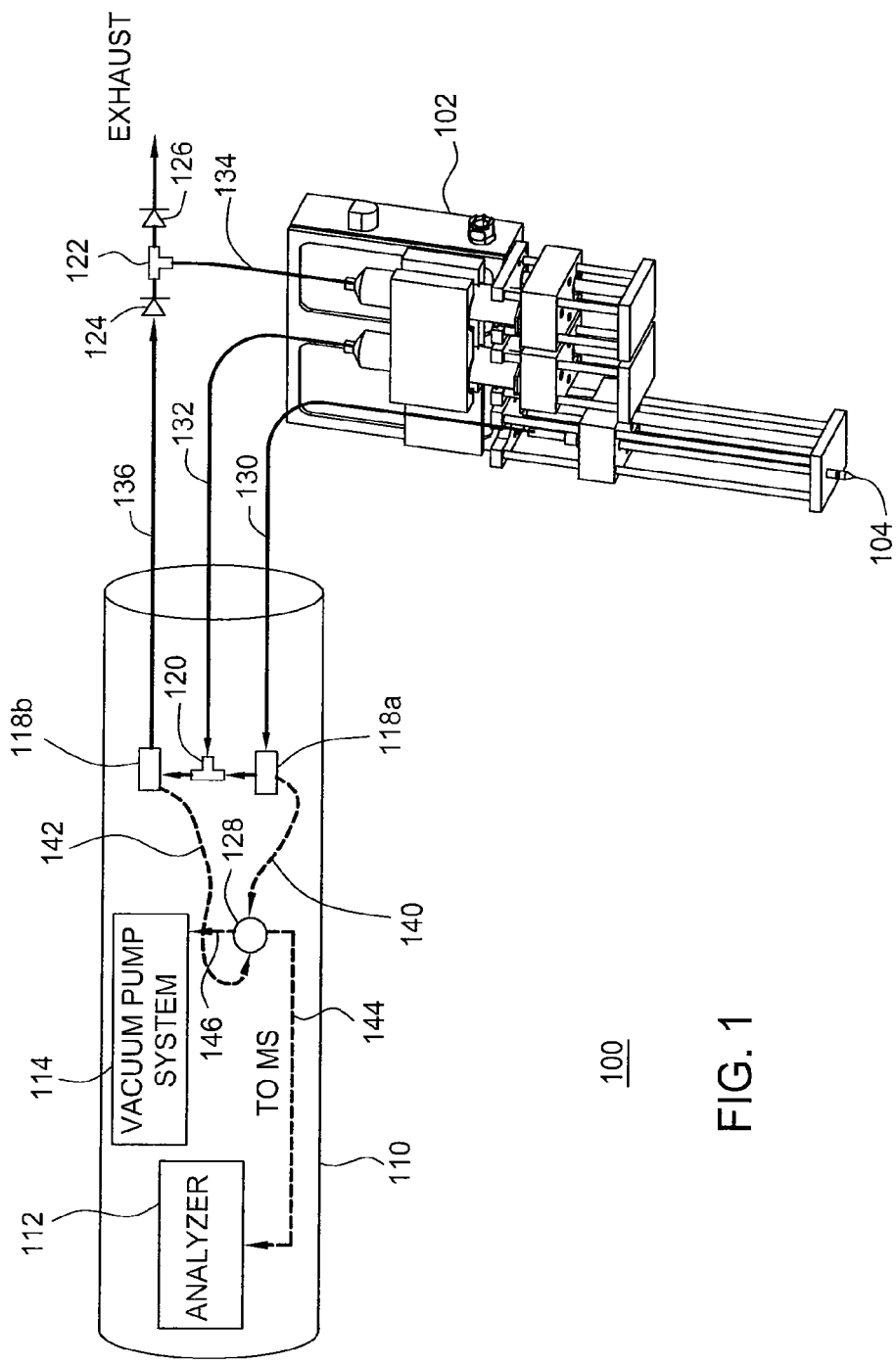
FIG. 1 illustrates a block diagram of one embodiment of a modular underwater sampling apparatus.

FIG. 1 illustrates a block diagram of one embodiment of an apparatus for obtaining a sample underwater 100. For example, the apparatus may be a module underwater sampling apparatus that can obtain samples in porewater or water in sediment. That is, the apparatus is a single device for collecting samples in deep seawater or fresh water and performing in-situ analysis and not a collection of different independent devices that may be found in a laboratory. Said another way, the apparatus 100 is designed to be a mobile apparatus for in-the-field use.

In one embodiment, the apparatus 100 comprises a sample pump and probe module 102 and an underwater analyzer module 110. The sample pump and probe module 102 includes a sampling probe 104. In one embodiment, the sample pump and probe module 102 may be a syringe pump that can withstand high pressures associated with underwater sampling.

In addition, the sample pump and probe module 102 provides a constant flow to the underwater analyzer module 110. For example, the sample pump and probe module 102 may provide a sample to the underwater analyzer module 110 at a rate of approximately 0.001 milliliters (mL) per minute (min) to 20.0 mL/min. It should be noted that the configuration and specification of the apparatus 100 may be any configuration and specification to provide a sample from the sample pump and probe module 102 to the underwater analyzer module 110 within the above range of flow rate. The flow rate is one factor in determining the accuracy of measurements and analysis performed by the underwater analyzer module 110.

In one embodiment, the underwater analyzer module 110 comprises an analyzer 112, a vacuum pump system 114 and one or more membrane inlet assemblies 118a and 118b. In one embodiment, the analyzer 112 may be a mass spectrometer (MS) analyzer. In one embodiment, the mass spectrometer analyzer may be a linear quadrupole mass filter, e.g., a Transpector 2 Residual Gas Analyzer manufactured by Inficon Inc. of Syracuse, N.Y. It should be noted that other types of analyzers may be used, e.g., analyzers based on ultraviolet-visible (UV-Vis) or infrared (IR) spectroscopy.

In one embodiment, the vacuum pump system 114 may include one or more pumps. For example, a combination of a rough pump and a turbo pump may be used. Alternatively, a single ion pump may be used. It should be noted that any combination or types of pumps may be used to create a vacuum draw and have the ability to exhaust samples in the lines to atmosphere.

In FIG. 1, the solid lines 130, 132, 134 and 136 represent a liquid phase sample flow or line. The dashed lines 140, 142, 144 and 146 represent a gas phase sample flow or line. In one embodiment, the sample may be drawn in via line 130 and fed to a first membrane inlet assembly 118a. The sample may be heated within the first membrane inlet assembly 118a and pervaporated through a semi-permeable membrane into a gas phase. The gas phase sample may then be fed to the analyzer 112 through a switch 128 and lines 140 and 144.

In one embodiment, the vacuum pump system 114 is used to create a vacuum draw within the underwater analyzer module 110. In addition, the vacuum pump system 114 may be used to evacuate the gas phase sample out of lines 140 and 142 when not being analyzed.

The apparatus 100 may provide additional in-situ analysis by providing a reagent (e.g., an acid) via line 132. For example, some determinations such as a measurement of total inorganic carbon or dissolved inorganic carbon (DIC) in a sample require an acidification of the sample. Using the present apparatus 100, one may obtain such measurements in-situ. When the analyzer 112 is ready to perform the analysis, the sample may be fed out of the first membrane inlet assembly 118a to a fluidic tee 120, where the sample is infused with a reagent via the reagent fed by line 132. The reagent infused sample is then fed to a second membrane inlet assembly 118b.

At the second membrane inlet assembly 118b, the reagent infused sample may be pervaporated within the second membrane inlet assembly 118b into a gas phase. The switch 128 may be positioned to feed the analyzer 112 with the reagent infused sample from the second membrane inlet assembly 118b via lines 142 and 144.

An exhaust line is provided within the apparatus 100 to flush the lines. In one embodiment, an exhaust line 136 may run from the second membrane inlet assembly 118b to a first check valve 124, a fluidic tee 122 and a second check valve 126. It should be noted that FIG. 1 illustrates only one possible configuration for a modular underwater sampling apparatus 100.

Figure 3:
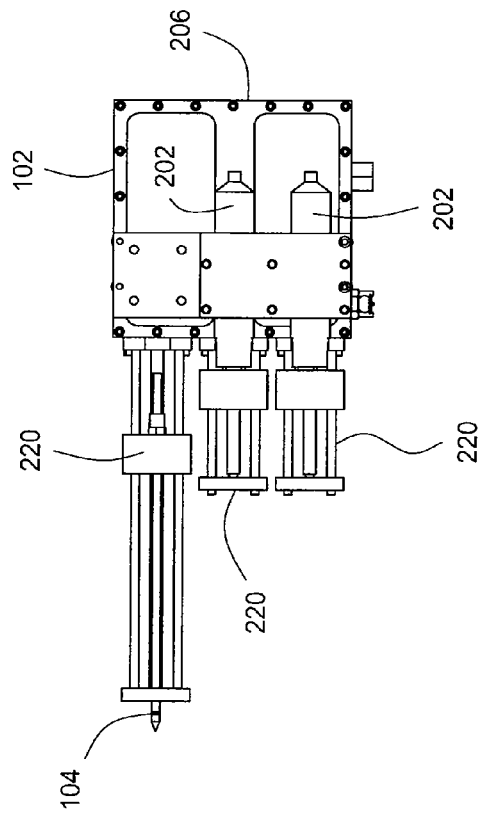
FIG. 3 illustrates a top view of the sample pump and probe of the modular underwater sampling apparatus.
Figure 2:
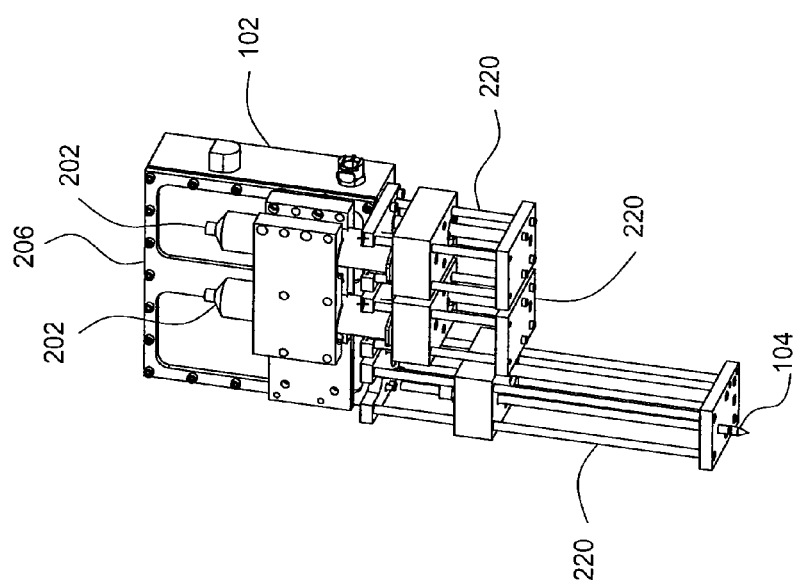
FIG. 2 illustrates an isometric view of a sample pump and probe of the modular underwater sampling apparatus.
Figure 4:
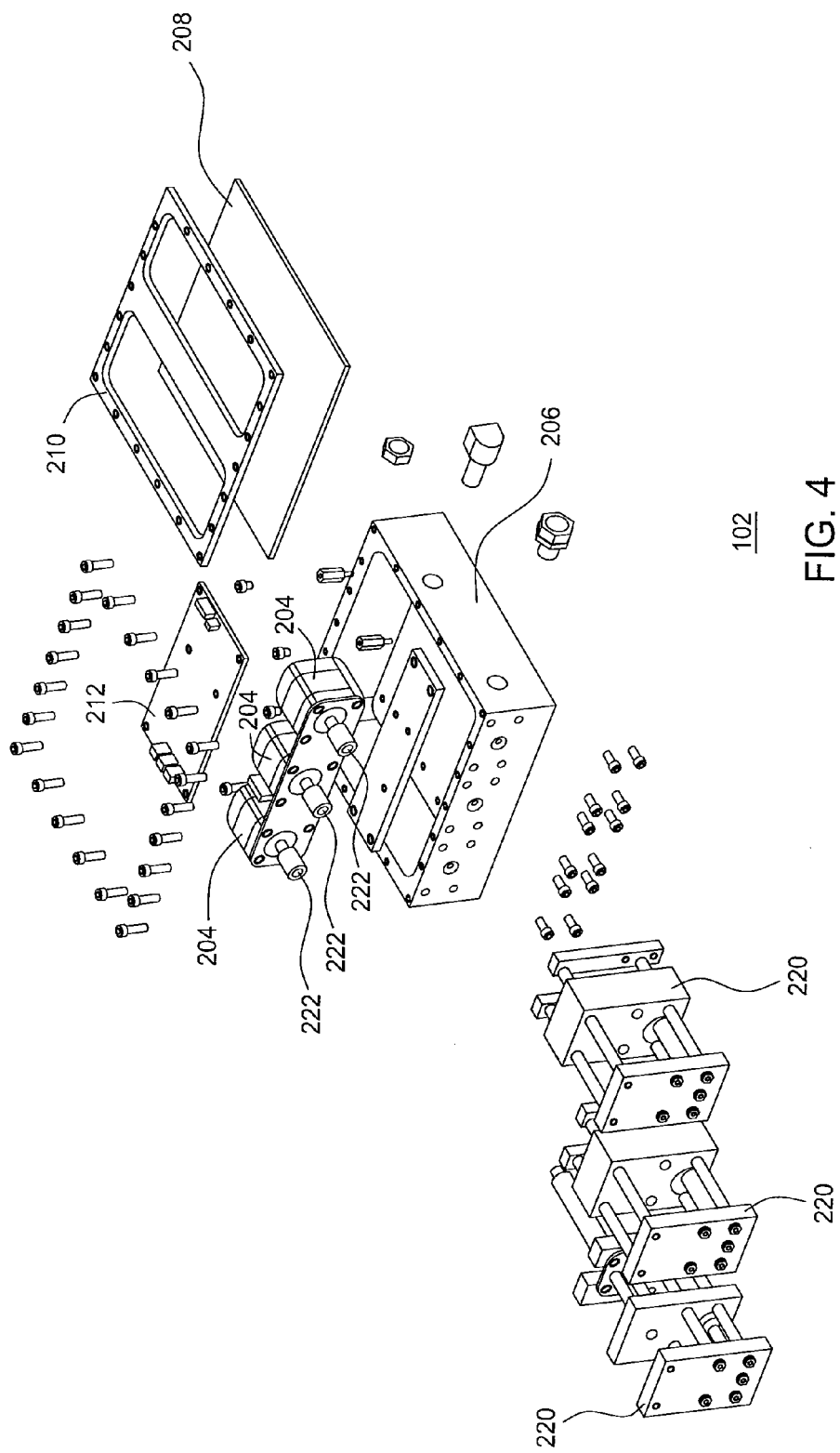
FIG. 4 illustrates an exploded view of the sample pump and probe of the modular underwater sampling apparatus.
Figure 5:
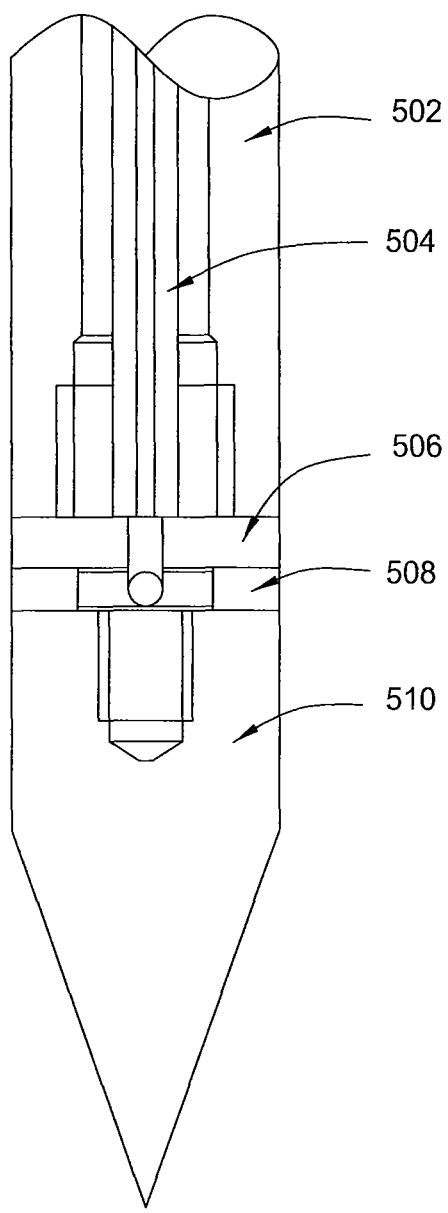
FIG. 5 illustrates a more detailed view of a probe used in the modular underwater sampling apparatus.

FIGS. 2, 3 and 4 illustrate more detailed views of the sample pump and probe module 102. FIG. 2 illustrates an isometric view of a fully assembled sample pump and probe module 102. In one embodiment, the sample pump and probe module 102 comprises a plurality of blocks 220 coupled to an oil filled box 206. The plurality of blocks 220 may be coupled to either a sampling probe 104 or a syringe 202. Notably, the sampling probe 104 and the syringe 202 are interchangeable in any one of the plurality of blocks 220. For example, the sampling probe 104 may replace one of the syringes 202. Any number of or combination of sampling probes 104 or syringes 202 may be used. It should be noted that although three blocks 220 are illustrated, the sample pump and probe module 102 may be fitted with any number of blocks 220 to hold any number of sampling probes 104 or syringes 202 required by a particular application. A more detailed view of the sampling probe 104 is illustrated in FIG. 5 and discussed below. FIG. 3 illustrates a top view of the sample pump and probe module 102.

FIG. 4 illustrates an exploded view of one embodiment of the sample pump and probe module 102. In one embodiment, the sample pump and probe module 102 comprises a plurality of stepper motors 204. The sample pump and probe module 102 may have an equal number of blocks 220 for holding a sampling probe 104 or a syringe 202 and stepper motors 204. Each block 220 is coupled to a stepper motor 204 for operating a sampling probe 104 or a syringe 202. It should be noted that operation of the blocks 220, and correspondingly either a sampling probe 104 or a syringe 202 coupled to a respective block 220, are not limited to a stepper motor 204. Any motor device may be used to operate the blocks 220, such as for example, a direct current (DC) motor.

In operation, motion is transferred via rotating leads 222 on the stepper motors 204 that are sealed by an o-ring. The rotating leads 222 drive a lead screw enabling lateral motion. This lateral motion is used to draw and plunge the blocks 220 to operating the sampling probe 104 or a syringe 202 or precisely control a sampling inlet location.

A printed circuit board (PCB) controller 212 is coupled to the stepper motors 204 and mounted on the oil filled box 206. In one embodiment, the PCB controller 212 is capable of multiple control protocols and used to control the operation of the stepper motors 204 and blocks 220. For example, the PCB controller 212 may be programmed to implement various sampling algorithms and/or instruct a syringe 202 in a block 220 to provide a reagent for infusing a sample with the reagent to the underwater analyzer module 110 for analysis. The rotating leads 222 may also be used to operate another motion device, for example a multi-position valve.

The oil filled box 206 is filled with oil or any other similar liquid. The oil is contained by an oil tolerant flexible sheet 208. The oil tolerant flexible sheet 208 allows ambient hydrostatic pressure to be transferred into the oil, while maintaining a positive overpressure ensuring the impossibility of seawater entering the system. The oil tolerant flexible sheet 208 is mounted onto the oil filled box 206 with a top cover 210. The components could also be housed inside a hard pressure vessel designed to withstand hydrostatic pressure at depth.

The design of the sample pump and probe module 102 allows the modular underwater sample pump 100 to operate at full ocean depths, e.g., up to 4000 meters (m), where pressure can be greater than 400 atmospheres (atm). Most components are outside of the oil filled box 206 allowing for easy modifications.

Another feature of the design of the sample pump and probe module 102 is that, at most, only coarse filters are required. Currently used designs require filters to be installed to prevent particulates in the sample from interfering with operation of the pumps. The design of the currently disclosed sample pump and probe module 102 provides immunity to particulate or sediment in the sample flow. The stepper motors 204 and drive leads or rotating leads 222 are not in contact with the sample. Rather, the stepper motors 204 simply provide the lateral motion to draw and plunge the syringes 202 or sampling probe 104 in blocks 220. In other words, no precision components are in contact with the flowing sample, hence particulates in the sample will not disrupt or alter sample flow.

In operation, using multiple syringes 202 allows one syringe 202 to draw fluid from a sample point, while a different syringe 202 plunges out a previous sampled fluid to get ready for the next draw. This allows for continuous flow operation. Alternatively, continuous flow operation may be achieved with a single motor 204 via a double action check valve mechanism. It should be noted that the configurations are only provided as examples and not considered limiting. Other configurations are within the scope of the present invention.

Another advantage of using a plurality of syringes 202 is that the sample pump and probe 102 may be used for flow injection analysis (FIA). For example, one of the syringes 202 may be deployed containing a reagent that could be injected into the sample stream. For example, the reagent could be an acid to acidify the sample for measurement of total inorganic carbon or DIC, as noted above with reference to FIG. 1.

FIG. 5 illustrates a more detailed view of one embodiment of the sampling probe 104. The sampling probe 104 is designed to provide millimeter sampling resolution capable of probing environments such as sediments, hydrate environments or vent fluids. These environments have very strong spatial chemical gradients that control the flux of important species including heavy metals, dissolved gases, volatile organic compounds and nutrients. In addition, the sampling probe 104 is designed to provide precision point sampling.

In one embodiment, the sampling probe 104 comprises a support tube 502, a sampling tube 504, a base 506, a sintered frit or disc 508 and a tip 510. The base 506 may hold all the parts together.

The tip 510 is designed with a pointed or angular tip for sediment penetration. In one embodiment, the tip 510 may be a machinable inert material, e.g., polyaryletheretherketone (PEEK) tip. In operation, after the tip 510 is inserted into a sampling point, the sample is drawn to the sintered disc or frit 508. In one embodiment the sintered disc or frit 508 provides a porous disc for sample intake. The sintered disc or frit 508 may be an inert porous material, e.g., a ceramic.

The sintered disc or frit 508 is coupled to the sampling tube 504. In one embodiment, the sampling tube 504 comprises small internal diameter (ID) tubing. The ID of the sampling tube 504 may be approximately 1/64". In one embodiment the sampling tube 504 outer diameter (OD) is approximately 1/16". In one embodiment, the sampling tube 504 comprises hastelloy C tubing, but could also be titanium or PEEK.

The sampling tube 504 is enclosed in a support tube 502. The support tube 502 may be fabricated from a hard material to protect the sampling tube 504. The ID of the support tube 502 is larger than the OD of the sampling tube 504. For example, if the OD of the sampling tube 504 is approximately 1/16", then the ID of the support tube 502 may be approximately 1/84". It should be noted that the IDs and ODs provided above are examples and that the ODs and IDs may be any length as not introduce an excessive delay in pumping the sample from the sampling probe to the analyzer 112.

Figure 6:
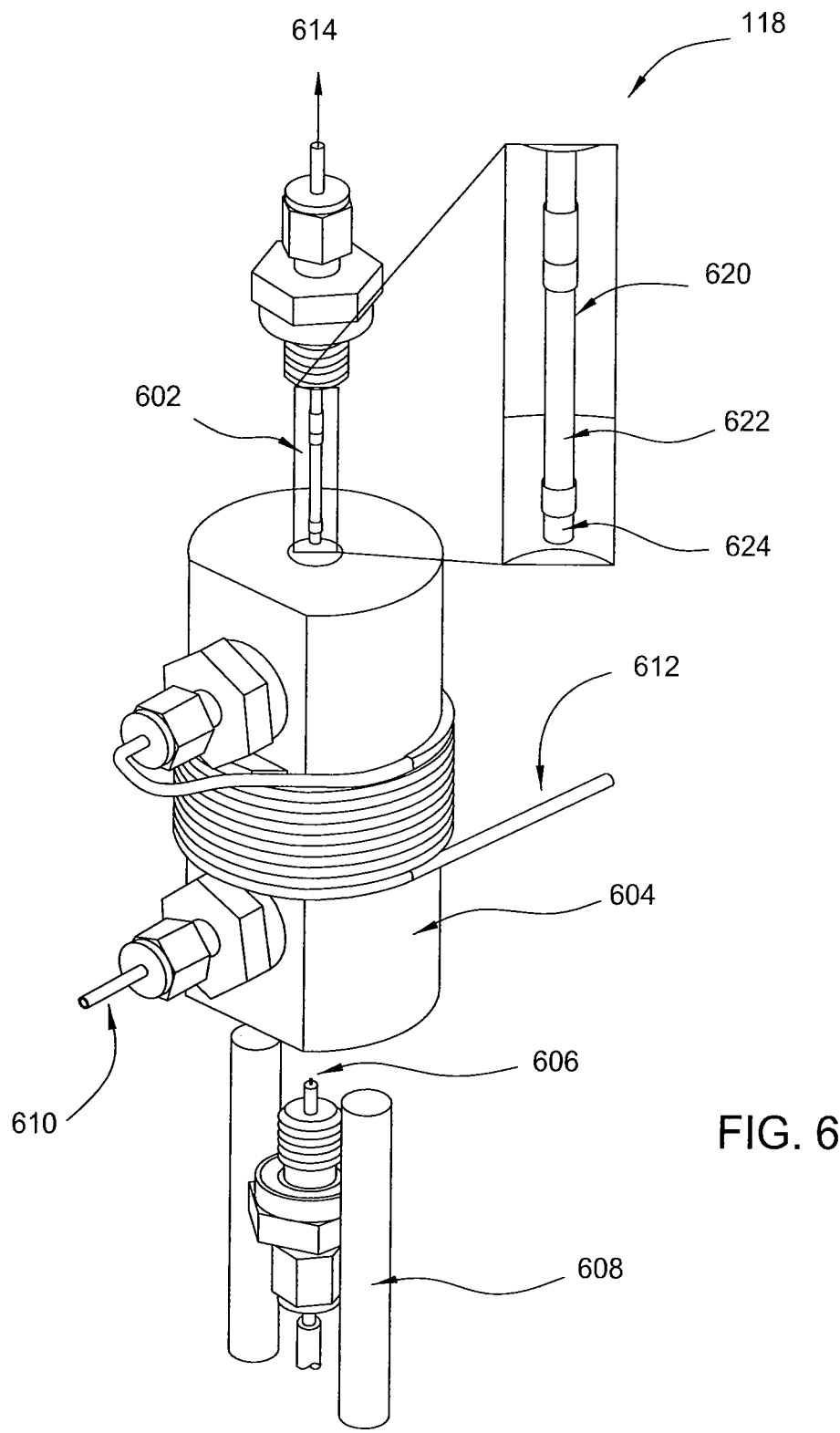
FIG. 6 illustrates a more detailed view of a membrane assembly used in a mass spectrometer module of the underwater sampling apparatus.

FIG. 6 illustrates a more detailed view of the membrane inlet assemblies 118a and 118b (herein collectively membrane inlet assembly 118). In one embodiment, the sample enters the membrane inlet assembly 118 via a sample inlet 612. The sample inlet is wrapped around a heater block 604 that is coupled to a thermocouple 606 and one or more heater cartridges 608.

As discussed above, the sample may be heated within the membrane inlet assembly 118 and pervaporated through a semi-permeable membrane into a gas phase. It should be noted that alternative designs of the modular underwater sampling apparatus 100 contemplate that the sample may be preheated before the sample enters the membrane inlet assembly 118. These alternate design modifications are also within the scope of the present invention. The gas phase sample may then be fed to the analyzer 112 directly or through a switch 128 and lines 140 and 144, as illustrated in FIG. 1.

As discussed above, in one embodiment the vacuum pump system 114 is used to create a vacuum draw in line 614. The vacuum draw 614 pulls the gas phase sample from a membrane interface 602 coupled to or inserted in the heater block 604.

The membrane interface 602 comprises a membrane 620, a sintered rod 622 and a cap 624. In one embodiment, the membrane 620 may comprise a polydimethylsiloxane (PDMS) membrane, the sintered rod 622 may be a porous sintered rod and the cap 624 may comprise a PEEK cap. For example, the PDMS membrane may be mounted in a stretched state on the porous sintered rod. The membrane interface 602 may be sealed with an epoxy or other similar polymer.

The remaining liquid phase sample may be exhausted from the membrane inlet assembly 118 via a sample outlet 610. As illustrated in FIG. 1, the sample outlet 610 may be used to exhaust the sample via line 136 or to carry the sample to fluidic tee 120 for acidification.

Thus, a modular underwater sampling apparatus is described herein. The modular design provides flexibility in easily swapping out the syringe or analyzers for specific applications. For example, the MS analyzer may be easily swapped out for other types of analyzers or optical detectors that relay on other analytical techniques, such as, spectrophotometry, fluorescence and chemiluminescence.

The modular design also isolates multiple fluid connections from sensitive electronic components, such as the MS analyzer. This minimizes potential damage from small water leaks within one or more of the modules.

The additional in-situ analysis provided by the modular underwater sampling allow the modular underwater sampling apparatus to be used for all aspects of aqueous studies, such as for example, vertical and horizontal mapping of chemical distribution, long term observations of chemical variability and deep sea studies.

The design of the modular underwater sampling apparatus provides ability to take samples at deep ocean depths, e.g., up to 4000 m depths, without degradation of pump performance due to increase in hydrostatic pressure. In other words, the present module underwater sampling apparatus is able to withstand the high ambient pressures at extreme ocean depths. Furthermore, the design of the modular underwater sampling apparatus allows for extended continuous operation, providing sufficient power is available.

In addition, the design of the disclosed modular underwater sampling apparatus provides flexibility in use in applications outside of underwater analysis. For example, the modular underwater sampling apparatus may be used in industrial process control or effluent monitoring.

While various embodiments have been described above, it should be understood that they have been presented by way of example only, and should not be considered limiting. Thus, the breadth and scope of a preferred embodiment should not be limited by any of the above-described exemplary embodiments, but should be defined only in accordance with the following claims and their equivalents.

What is claimed is:

1. An apparatus for obtaining a sample underwater, comprising:
 a syringe pump comprising a plurality of blocks, at least one syringe coupled to at least one of said plurality of blocks and at least one sampling probe coupled to a different at least one of said plurality of blocks for collecting said sample underwater; and
 an analyzer module coupled to said syringe pump, wherein said at least one sampling probe comprises:
  an angular tip coupled to a base;
  a sintered disc coupled between said angular tip and said base;
  a support tube coupled to said base; and
  a sampling tube coupled to said base within said support tube.

2. The apparatus of claim 1, wherein said angular tip and said base comprise a polyaryletheretherketone (PEEK).

3. The apparatus of claim 1, wherein said syringe pump comprises:
 an oil filled box;
 a motor coupled to each of said plurality of blocks and said oil filled box; and
 a controller coupled to said oil filled box.

4. The apparatus of claim 1, wherein said syringe pump provides said sample to said analyzer module at a constant flow of approximately 0.001 milliliters (mL) per minute (min) to 20.0 mL/min.

5. The apparatus of claim 1, wherein said at least one syringe provides a reagent to be added to a sample collected by said at least one sampling probe.

6. An apparatus for obtaining a sample underwater, comprising:
 a syringe pump comprising a plurality of blocks, at least one syringe coupled to at least one of said plurality of blocks and at least one sampling probe coupled to a different at least one of said plurality of blocks for collecting said sample underwater; and
 an analyzer module coupled to said syringe pump, wherein said analyzer module comprises:
  an analyzer;
  at least one membrane inlet assembly coupled to said analyzer; and
  a vacuum pump system coupled to said analyzer and said at least one membrane inlet assembly.

7. The apparatus of claim 6, wherein said at least one membrane inlet assembly comprises:
 a heater block;
 a sample inlet coupled to said heater block;
 a sample outlet coupled to said heater block;
 a heater cartridge coupled to said heater block;
 a thermocouple coupled to said heater block;
 a membrane interface coupled to said heater block; and
 a vacuum outlet coupled to said membrane.

8. The apparatus of claim 7, wherein said membrane interface comprises:
 a polydimethylsiloxane (PDMS) membrane;
 a sintered rod coupled to said PDMS membrane; and
 a polyaryletheretherketone (PEEK) cap coupled to said sintered rod.

9. The apparatus of claim 6, wherein said at least one membrane inlet assembly comprises two membrane inlet assemblies coupled to one another via a fluidic tee.

10. The apparatus of claim 7, wherein said syringe pump comprises:
 an oil filled box;
 a motor coupled to each of said plurality of blocks and said oil filled box; and
 a controller coupled to said oil filled box.

11. The apparatus of claim 6, wherein said syringe pump provides said sample to said analyzer module at a constant flow of approximately 0.001 milliliters (mL) per minute (min) to 20.0 mL/min.

12. The apparatus of claim 6, wherein said at least one syringe provides a reagent to be added to a sample collected by said at least one sampling probe.

* * * * *